United States Patent
Bourget et al.

(10) Patent No.: US 6,939,970 B2
(45) Date of Patent: Sep. 6, 2005

(54) CRYSTALLINE FORM OF (3R,4R)-4-[3-(S)-HYDROXY-3-(6 METHOXYQUINOLIN-4-PROPYL]-1-[2-2-THIENYLTHIO)ETHYL] PIPERIDINE-3-CARBOXYLIC ACID

(75) Inventors: Jacques Bourget, Vitry sur Seine (FR); Marc Antoine Perrin, Jouy en Josas (FR); Bernd Janocha, Wiesbaden (DE); Carole Neves, Paris (FR); Pascal Billot, Montreuil (FR); Sylvaine Lafont, Trevoux (FR)

(73) Assignee: Aventis Pharma S. A., Antony (FR)

( * ) Notice: Subject to any disclaimer, the term of this patent is extended or adjusted under 35 U.S.C. 154(b) by 5 days.

(21) Appl. No.: 10/739,704

(22) Filed: Dec. 18, 2003

(65) Prior Publication Data
US 2004/0147554 A1 Jul. 29, 2004

Related U.S. Application Data
(60) Provisional application No. 60/479,602, filed on Jun. 18, 2003.

(30) Foreign Application Priority Data
Dec. 20, 2002 (FR) .............................. 02 16418

(51) Int. Cl.[7] .................... C07D 215/12; C07D 215/18; A61K 31/47
(52) U.S. Cl. ...................... 546/174; 546/177; 546/178; 546/180; 514/314; 514/311
(58) Field of Search ................ 514/314, 311; 546/174, 177, 178, 180

(56) References Cited
U.S. PATENT DOCUMENTS 6,403,610 B1 * 6/2002 Malleron et al. ........... 514/314
6,602,884 B2 * 8/2003 Bacque et al. .............. 514/314

2004/0147751 A1   7/2004   Bourget

* cited by examiner

Primary Examiner—D. Margaret Seaman
(74) Attorney, Agent, or Firm—Balaram Gupta

(57) ABSTRACT

The present invention comprises monohydrated form C of (3R,4R)-4-[3-(S)-hydroxy-3-(6-methoxyquinolin-4-yl)propyl]-1-[2-(2-thienylthio)ethyl]piperidine-3-carboxylic acid, represented by the structure

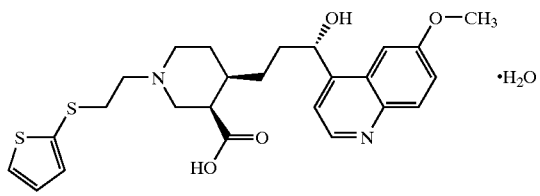

and as herein defined by powder X-ray diffraction, processes for preparing monohydrated form C from amorphorous (3R,4R)-4-[3-(S)-hydroxy-3-(6-methoxyquinolin-4-yl)propyl]-1-[2-(2-thienylthio)ethyl]piperidine-3-carboxylic acid or form A of (3R,4R)-4-[3-(S)-hydroxy-3-(6-methoxyquinolin-4-yl)propyl]-1-[2-(2-thienylthio)ethyl]piperidine-3-carboxylic acid, pharmaceutical compositions comprising monohydrated form C, pharmaceutical compositions comprising monohydrated form C and form A or form B of (3R,4R)-4-[3-(S)-hydroxy-3-(6-methoxyquinolin-4-yl)propyl]-1-[2-(2-thienylthio)ethyl]piperidine-3-carboxylic acid, pharmaceutical compositions comprising monohydrated form C, form A and form B, methods for treating bacterial infection with monohydrated form C, methods for treating bacterial infection with monohydrated form C and form A or form B, methods for treating bacterial infection with monohydrated form C, form A and form B, and a process for the preparation of form A from monohydrated form C.

21 Claims, No Drawings

CRYSTALLINE FORM OF (3R,4R)-4-[3-(S)-HYDROXY-3-(6 METHOXYQUINOLIN-4-PROPYL]-1-[2-2-THIENYLTHIO)ETHYL] PIPERIDINE-3-CARBOXYLIC ACID

This application claims priority from French patent application number 0216418, filed Dec. 20, 2002, and the benefit of U.S. Provisional Application No. 60/479,602, filed Jun. 18, 2003.

BACKGROUND OF THE INVENTION

1. Field of the Invention

The present invention relates to a crystalline form of (3R,4R)-4-[3-(S)-hydroxy-3-(6-methoxyquinolin-4-yl)propyl]-1-[2-(2-thienylthio)ethyl]piperidine-3-carboxylic acid, represented by the structure:

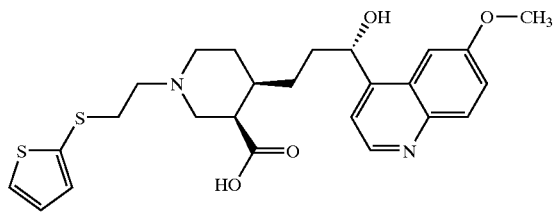

2. Description of the Art (3R,4R)-4-[3-Hydroxy-3-(6-methoxyquinolin-4-yl)propyl]-1-[2-(2-thienylthio)-ethyl]piperidine-3-carboxylic acid and its preparation has been disclosed in U.S. Pat. No. 6,403,610, the disclosure of which is hereby incorporated by reference, in the form of 2 diastereoisomers, known as diastereoisomer A and diastereoisomer B. In U.S. Pat. No. 6,403,610, the diastereoisomers obtained existed in the amorphous form. Among the diastereoisomers of this quinolylpropylpiperidine derivative, diastereoisomer A, (3R,4R)-4-[3-(S)-hydroxy-3-(6-methoxyquinolin-4-yl)propyl]-1-[2-(2-thienylthio)ethyl]piperidine-3-carboxylic acid, is particularly advantageous for its antibacterial activity, in particular with regard to microorganisms such as *Staphylococcus aureus, Streptococcus pneumoniae, Enterococcus faecium* or *Moraxella catharrhalis*. It is also highly advantageous because of its good activity, both by the oral route and by the injectable route, and because of its low toxicity.

SUMMARY OF THE INVENTION

The present invention comprises monohydrated form C of (3R,4R)-4-[3-(S)-hydroxy-3-(6-methoxyquinolin-4-yl)propyl]-1-[2-(2-thienylthio)ethyl]piperidine-3-carboxylic acid, represented by the structure

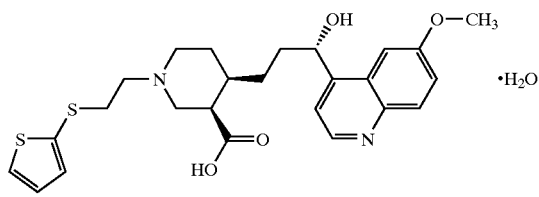

and as herein defined by powder X-ray diffraction pattern, a process for preparing monohydrated form C of (3R,4R)-4-[3-(S)-hydroxy-3-(6-methoxyquinolin-4-yl)propyl]-1-[2-(2-thienylthio)ethyl]piperidine-3-carboxylic acid from amorphous (3R,4R)-4-[3-(S)-hydroxy-3-(6-methoxyquinolin-4-yl)propyl]-1-[2-(2-thienylthio)ethyl]piperidine-3-carboxylic acid, a process for preparing monohydrated form C of (3R,4R)-4-[3-(S)-hydroxy-3-(6-methoxyquinolin-4-yl)propyl]-1-[2-(2-thienylthio)ethyl]piperidine-3-carboxylic acid from form A of (3R,4R)-4-[3-(S)-hydroxy-3-(6-methoxyquinolin-4-yl)propyl]-1-[2-(2-thienylthio)ethyl]-piperidine-3-carboxylic acid, a pharmaceutical composition comprising monohydrated form C of (3R,4R)-4-[3-(S)-hydroxy-3-(6-methoxyquinolin-4-yl)propyl]-1-[2-(2-thienylthio)ethyl]-piperidine-3-carboxylic acid, a pharmaceutical composition comprising monohydrated form C of (3R,4R)-4-[3-(S)-hydroxy-3-(6-methoxyquinolin-4-yl)propyl]-1-[2-(2-thienylthio)ethyl]-piperidine-3-carboxylic acid and form A of (3R,4R)-4-[3-(S)-hydroxy-3-(6-methoxyquinolin-4-yl)propyl]-1-[2-(2-thienylthio)ethyl]piperidine-3-carboxylic acid or form B of (3R,4R)-4-[3-(S)-hydroxy-3-(6-methoxyquinolin-4-yl)propyl]-1-[2-(2-thienylthio)ethyl]-piperidine-3-carboxylic acid, a pharmaceutical composition comprising monohydrated form C of (3R,4R)-4-[3-(S)-hydroxy-3-(6-methoxyquinolin-4-yl)propyl]-1-[2-(2-thienylthio)ethyl]piperidine-3-carboxylic acid, form A of (3R,4R)-4-[3-(S)-hydroxy-3-(6-methoxyquinolin-4-yl)propyl]-1-[2-(2-thienylthio)ethyl]piperidine-3-carboxylic acid and form B of (3R,4R)-4-[3-(S)-hydroxy-3-(6-methoxyquinolin-4-yl)propyl]-1-[2-(2-thienylthio)ethyl]piperidine-3-carboxylic acid; a method for treating bacterial infections with monohydrated form C of (3R,4R)-4-[3-(S)-hydroxy-3-(6-methoxyquinolin-4-yl)propyl]-1-[2-(2-thienylthio)ethyl]piperidine-3-carboxylic acid, a method for treating bacterial infections with monohydrated form C of (3R,4R)-4-[3-(S)-hydroxy-3-(6-methoxyquinolin-4-yl)propyl]-1-[2-(2-thienylthio)ethyl]-piperidine-3-carboxylic acid and form A of (3R,4R)-4-[3-(S)-hydroxy-3-(6-methoxyquinolin-4-yl)propyl]-1-[2-(2-thienylthio)ethyl]-piperidine-3-carboxylic acid or form B of (3R,4R)-4-[3-(S)-hydroxy-3-(6-methoxyquinolin-4-yl)propyl]-1-[2-(2-thienylthio)ethyl]piperidine-3-carboxylic acid; a method for treating bacterial infection with monohydrated form C of (3R,4R)-4-[3-(S)-hydroxy-3-(6-methoxyquinolin-4-yl)propyl]-1-[2-(2-thienylthio)ethyl]piperidine-3-carboxylic acid, form A of (3R,4R)-4-[3-(S)-hydroxy-3-(6-methoxyquinolin-4-yl)propyl]-1-[2-(2-thienylthio)ethyl]piperidine-3-carboxylic acid and form B of (3R,4R)-4-[3-(S)-hydroxy-3-(6-methoxyquinolin-4-yl)propyl]-1-[2-(2-thienylthio)ethyl]piperidine-3-carboxylic acid, and a process for preparing form A of (3R,4R)-4-[3-(S)-hydroxy-3-(6-methoxyquinolin-4-yl)propyl]-1-[2-(2-thienylthio)ethyl]piperidine-3-carboxylic acid from monohydrated form C of 3R,4R)-4-[3-(S)-hydroxy-3-(6-methoxyquinolin-4-yl)propyl]-1-[2-(2-thienylthio)ethyl]piperidine-3-carboxylic acid.

Accordingly one embodiment of this invention is directed to monohydrated form C of (3R,4R)-4-[3-(S)-hydroxy-3-(6-methoxyquinolin-4-yl)propyl]-1-[2-(2-thienylthio)ethyl] piperidine-3-carboxylic acid as herein defined by powder X-ray diffraction pattern.

Another embodiment of this invention is directed to a process for the preparation of monohydrated form C of (3R,4R)-4-[3-(S)-hydroxy-3-(6-methoxyquinolin-4-yl)propyl]-1-[2-(2-thienylthio)ethyl]piperidine-3-carboxylic acid comprising the steps of dissolving amorphous (3R,4R)-4-[3-(S)-hydroxy-3-(6-methoxyquinolin-4-yl)propyl]-1-[2-(2-thienylthio)ethyl]piperidine-3-carboxylic acid in a mixture of water and a water-miscible organic solvent to provide a saturated solution, and evaporating said solution at 20° C. to 25° C. over a suitable period of time.

Yet another embodiment of this invention is a process for the preparation of monohydrated form C of (3R,4R)-4-[3-

(S)-hydroxy-3-(6-methoxyquinolin-4-yl)propyl]-1-[2-(2-thienylthio)ethyl]piperidine-3-carboxylic acid comprising the step of stirring a suspension of form A of (3R,4R)-4-[3-(S)-hydroxy-3-(6-methoxy-quinolin-4-yl)propyl]-1-[2-(2-thienylthio)ethyl]-piperidine-3-carboxylic acid in a mixture of water and a water-miscible organic solvent at 20° C. to 25° C. for a suitable period of time.

A further embodiment of this invention is directed to a pharmaceutical composition comprising monohydrated form C of (3R,4R)-4-[3-(S)-hydroxy-3-(6-methoxyquinolin-4-yl)propyl]-1-[2-(2-thienylthio)ethyl]piperidine-3-carboxylic acid and one or more pharmaceutically acceptable adjuvants or diluents.

Another embodiment of this invention is directed to a pharmaceutical composition comprising monohydrated form C of (3R,4R)-4-[3-(S)-hydroxy-3-(6-methoxyquinolin-4-yl)propyl]-1-[2-(2-thienylthio)ethyl]piperidine-3-carboxylic acid and form A of (3R,4R)-4-[3-(S)-hydroxy-3-(6-methoxyquinolin-4-yl)propyl]-1-[2-(2-thienylthio)ethyl]piperidine-3-carboxylic acid or form B of (3R,4R)-4-[3-(S)-hydroxy-3-(6-methoxyquinolin-4-yl)propyl]-1-[2-(2-thienylthio)ethyl]piperidine-3-carboxylic acid, and one or more pharmaceutically acceptable adjuvants or diluents.

A further embodiment of this invention is directed to a pharmaceutical composition comprising monohydrated form C of (3R,4R)-4-[3-(S)-hydroxy-3-(6-methoxyquinolin-4-yl)propyl]-1-[2-(2-thienylthio)ethyl]piperidine-3-carboxylic acid, form A of (3R,4R)-4-[3-(S)-hydroxy-3-(6-methoxyquinolin-4-yl)propyl]-1-[2-(2-thienylthio)ethyl]piperidine-3-carboxylic acid, and form B of (3R,4R)-4-[3-(S)-hydroxy-3-(6-methoxyquinolin-4-yl)propyl]-1-[2-(2-thienylthio)ethyl]piperidine-3-carboxylic acid and one or more pharmaceutically acceptable adjuvants or diluents.

Another embodiment of this invention is directed to a method for treating a bacterial infection comprising administering to a patient in need of said treatment a therapeutically effective amount of monohydrated form C of 3R,4R)-4-[3-(S)-hydroxy-3-(6-methoxyquinolin-4-yl)propyl]-1-[2-(2-thienylthio)ethyl]piperidine-3-carboxylic acid.

Another embodiment of this invention is directed to a method for treating a bacterial infection comprising administering to a patient in need of said treatment a therapeutically effective amount of monohydrated form C of 3R,4R)-4-[3-(S)-hydroxy-3-(6-methoxyquinolin-4-yl)propyl]-1-[2-(2-thienylthio)ethyl]piperidine-3-carboxylic acid and form A of 3R,4R)-4-[3-(S)-hydroxy-3-(6-methoxyquinolin-4-yl)propyl]-1-[2-(2-thienylthio)ethyl]piperidine-3-carboxylic acid or form B of 3R,4R)-4-[3-(S)-hydroxy-3-(6-methoxyquinolin-4-yl)propyl]-1-[2-(2-thienylthio)ethyl]piperidine-3-carboxylic acid.

A further embodiment of this invention is directed to a method for treating a bacterial infection comprising administering to a patient in need of said treatment a therapeutically effective amount of monohydrated form C of 3R,4R)-4-[3-(S)-hydroxy-3-(6-methoxyquinolin-4-yl)propyl]-1-[2-(2-thienylthio)ethyl]-piperidine-3-carboxylic acid, form A of 3R,4R)-4-[3-(S)-hydroxy-3-(6-methoxy-quinolin-4-yl)propyl]-1-[2-(2-thienylthio)ethyl]piperidine-3-carboxylic acid and form B of 3R,4R)-4-[3-(S)-hydroxy-3-(6-methoxyquinolin-4-yl)propyl]-1-[2-(2-thienylthio)ethyl]piperidine-3-carboxylic acid.

Another embodiment of this invention is directed to a process for the preparation of form A of 3R,4R)-4-[3-(S)-hydroxy-3-(6-methoxyquinolin-4-yl)propyl]-1-[2-(2-thienylthio)ethyl]piperidine-3-carboxylic acid from monohydrated form C of 3R,4R)-4-[3-(S)-hydroxy-3-(6-methoxyquinolin-4-yl)propyl]-1-[2-(2-thienylthio)ethyl] piperidine-3-carboxylic acid comprising drying said monohydrated form C below 50% humidity to provide form B of (3R,4R)-4-[3-(S)-hydroxy-3-(6-methoxyquinolin-4-yl)propyl]-1-[2-(2-thienylthio)ethyl]-piperidine-3-carboxylic acid, and then heating said form B at a temperature from about 148° C. to about 155° C. to provide form A of 3R,4R)-4-[3-(S)-hydroxy-3-(6-methoxyquinolin-4-yl)propyl]-1-[2-(2-thienylthio)ethyl]piperidine-3-carboxylic acid.

DETAILED DESCRIPTION OF THE INVENTION

The monohydrated crystalline form of (3R,4R)-4-[3-(S)-hydroxy-3-(6-methoxyquinolin-4-yl)propyl]-1-[2-(2-thienylthio)ethyl]piperidine-3-carboxylic acid, according to the invention, known hereinbelow as form C, has been defined by the indexing of its powder X-ray diffraction pattern diagram described hereinbelow.

Powder X-Ray Diffraction

The analyses are carried out on a Bruker D8 diffractometer having a copper-anticathode tube equipped with a front monochromator (wavelength of the copper K$\alpha_1$ line: 1.54060 Å). The arrangement is of Bragg-Brentano type, with a point scintillation detector. The angular range swept extends from 2 to 40 degrees 2θ with a step of 0.02 degrees 2θ. The counting time is 120 seconds per step.

The indexing of the form C is carried out at a temperature (T) of 295 K from a high-resolution powder X-ray diffraction diagram. The unit cell is orthorhombic (space group $P2_12_12_1$, Z=4). The parameters are as follows:

a=20.0224 Å α=β=γ=90°
b=11.6071 Å
c=11.0255 Å V=2562.36 Å$^3$

The asymmetric unit cell is composed of a molecule of (3R,4R)-4-[3-(S)-hydroxy-3-(6-methoxyquinolin-4-yl)propyl]-1-[2-(2-thienylthio)ethyl]piperidine-3-carboxylic acid and a molecule of water.

The complete indexing of the lines of the powder X-ray diffraction diagram of form C of (3R,4R)-4-[3-(S)-hydroxy-3-(6-methoxyquinolin-4-yl)propyl]-1-[2-(2-thienylthio)-ethyl]piperidine-3-carboxylic acid at T=295 K, in lattice spacing and in "mean $\lambda_{Cu\ K\alpha}$"2θ positions, gives the following result:

| | | | | Form C | |
|---|---|---|---|---|---|
| h | k | l | Multiplicity factor J | Lattice spacing (Å) | 2θ "mean $\lambda_{C_uK\alpha}$" 1.54184 Å |
| 1 | 1 | 0 | 4 | 10.0418 | 8.8058 |
| 2 | 0 | 0 | 2 | 10.0112 | 8.8327 |
| 1 | 0 | 1 | 4 | 9.6580 | 9.1564 |
| 0 | 1 | 1 | 4 | 7.9939 | 11.0679 |
| 2 | 1 | 0 | 4 | 7.5809 | 11.6729 |
| 1 | 1 | 1 | 8 | 7.4241 | 11.9204 |
| 2 | 0 | 1 | 4 | 7.4117 | 11.9404 |
| 2 | 1 | 1 | 8 | 6.2468 | 14.1776 |
| 0 | 2 | 0 | 2 | 5.8035 | 15.2666 |
| 3 | 1 | 0 | 4 | 5.7858 | 15.3136 |
| 3 | 0 | 1 | 4 | 5.7095 | 15.5195 |
| 1 | 2 | 0 | 4 | 5.5741 | 15.8990 |
| 0 | 0 | 2 | 2 | 5.5128 | 16.0771 |
| 1 | 0 | 2 | 4 | 5.3150 | 16.6795 |
| 0 | 2 | 1 | 4 | 5.1355 | 17.2667 |
| 3 | 1 | 1 | 8 | 5.1233 | 17.3084 |
| 2 | 2 | 0 | 4 | 5.0209 | 17.6641 |

-continued

Form C

| h | k | l | Multiplicity factor J | Lattice spacing (Å) | 2θ "mean λ_{CuKα}" 1.54184 Å |
|---|---|---|---|---|---|
| 4 | 0 | 0 | 2 | 5.0056 | 17.7185 |
| 0 | 1 | 2 | 4 | 4.9796 | 17.8116 |
| 1 | 2 | 1 | 8 | 4.9745 | 17.8301 |
| 1 | 1 | 2 | 8 | 4.8324 | 18.3588 |
| 2 | 0 | 2 | 4 | 4.8290 | 18.3719 |
| 4 | 1 | 0 | 4 | 4.5964 | 19.3104 |
| 2 | 2 | 1 | 8 | 4.5694 | 19.4256 |
| 4 | 0 | 1 | 4 | 4.5579 | 19.4752 |
| 2 | 1 | 2 | 8 | 4.4585 | 19.9134 |
| 3 | 2 | 0 | 4 | 4.3794 | 20.2770 |
| 3 | 0 | 2 | 4 | 4.2503 | 20.8996 |
| 4 | 1 | 1 | 8 | 4.2425 | 20.9387 |
| 3 | 2 | 1 | 8 | 4.0701 | 21.8363 |

Form C of (3R,4R)-4-[3-(S)-hydroxy-3-(6-methoxyquinolin-4-yl)propyl]-1-[2-(2-thienylthio)ethyl]piperidine-3-carboxylic acid is a monohydrate form. It is stable at 25° C. and at the degree of ambient humidity. It is particularly stable between 50% and 100% humidity. At 97% humidity, at 20° C., examination by powder X-ray diffraction shows stability in the monohydrate form after 11 weeks.

Below 50% humidity, a loss in mass of 3.7% by weight is recorded between 25° C. and 75° C. (1 mole of water/mole of the acid). This loss in mass corresponds to the dehydration of the form C to give another form of (3R,4R)-4-[3-(S)-hydroxy-3-(6-methoxyquinolin-4-yl)propyl]-1-[2-(2-thienylthio)ethyl]piperidine-3-carboxylic acid, hereinafter known as form B.

Form B is anhydrous, it is stable up to 30% humidity, it exhibits melting beginning at 147.6° C.–148° C., and then changes to an anhydrous form, known hereinbelow as form A, which recrystallizes at about 153° C.–155° C.

Thus, under another aspect of the present invention, form C can be used for the preparation of crystalline form A.

Forms B and A are defined, respectively, by the indexing of their powder X-ray diffraction pattern diagrams.

Form B

| h | k | l | Multiplicity factor J | Lattice spacing (Å) | 2θ "mean λ_{CuKα}" 1.54184 Å |
|---|---|---|---|---|---|
| 1 | 1 | 0 | 4 | 10.7550 | 8.2207 |
| 2 | 0 | 0 | 2 | 9.6616 | 9.1530 |
| 1 | 0 | 1 | 4 | 8.8988 | 9.9395 |
| 0 | 1 | 1 | 4 | 7.9263 | 11.1627 |
| 2 | 1 | 0 | 4 | 7.7429 | 11.4279 |
| 1 | 1 | 1 | 8 | 7.3333 | 12.0685 |
| 2 | 0 | 1 | 4 | 6.9567 | 12.7244 |
| 0 | 2 | 0 | 2 | 6.4728 | 13.6801 |
| 1 | 2 | 0 | 4 | 6.1376 | 14.4311 |
| 2 | 1 | 1 | 8 | 6.1280 | 14.4540 |
| 3 | 1 | 0 | 4 | 5.7667 | 15.3648 |
| 0 | 2 | 1 | 4 | 5.4378 | 16.3001 |
| 3 | 0 | 1 | 4 | 5.4190 | 16.3573 |
| 2 | 2 | 0 | 4 | 5.3775 | 16.4842 |
| 1 | 2 | 1 | 8 | 5.2345 | 16.9378 |
| 0 | 0 | 2 | 2 | 5.0125 | 17.6937 |
| 3 | 1 | 1 | 8 | 4.9987 | 17.7432 |
| 1 | 0 | 2 | 4 | 4.8520 | 18.2843 |
| 4 | 0 | 0 | 2 | 4.8308 | 18.3652 |
| 2 | 2 | 1 | 8 | 4.7388 | 18.7247 |
| 0 | 1 | 2 | 4 | 4.6744 | 18.9852 |
| 3 | 2 | 0 | 4 | 4.5657 | 19.4415 |

-continued

Form B

| h | k | l | Multiplicity factor J | Lattice spacing (Å) | 2θ "mean λ_{CuKα}" 1.54184 Å |
|---|---|---|---|---|---|
| 1 | 1 | 2 | 8 | 4.5433 | 19.5381 |
| 4 | 1 | 0 | 4 | 4.5259 | 19.6140 |
| 2 | 0 | 2 | 4 | 4.4494 | 19.9549 |
| 4 | 0 | 1 | 4 | 4.3519 | 20.4067 |

Form A

| h | k | l | Multiplicity factor J | Lattice spacing (Å) | 2θ "mean λ_{CuKα}" 1.54184 Å |
|---|---|---|---|---|---|
| 1 | 0 | 0 | 2 | 14.4954 | 6.0971 |
| 0 | 0 | 1 | 2 | 10.9797 | 8.0523 |
| -1 | 0 | 1 | 2 | 10.0030 | 8.8400 |
| 1 | 0 | 1 | 2 | 7.8775 | 11.2320 |
| 2 | 0 | 0 | 2 | 7.2477 | 12.2116 |
| -2 | 0 | 1 | 2 | 6.8662 | 12.8930 |
| 1 | 1 | 0 | 4 | 6.7356 | 13.1440 |
| 0 | 1 | 1 | 4 | 6.2527 | 14.1640 |
| -1 | 1 | 1 | 4 | 6.0549 | 14.6294 |
| -1 | 0 | 2 | 2 | 5.6060 | 15.8078 |
| 0 | 0 | 2 | 2 | 5.4898 | 16.1447 |
| 1 | 1 | 1 | 4 | 5.4720 | 16.1977 |
| 2 | 0 | 1 | 2 | 5.4674 | 16.2112 |
| 2 | 1 | 0 | 4 | 5.2472 | 16.8964 |
| -2 | 1 | 1 | 4 | 5.0969 | 17.3987 |
| -2 | 0 | 2 | 2 | 5.0015 | 17.7331 |
| -3 | 0 | 1 | 2 | 4.8826 | 18.1687 |
| 3 | 0 | 0 | 2 | 4.8318 | 18.3612 |
| 1 | 0 | 2 | 2 | 4.7641 | 18.6246 |
| -1 | 1 | 2 | 4 | 4.5129 | 19.6713 |
| 0 | 1 | 2 | 4 | 4.4516 | 19.9449 |
| 2 | 1 | 1 | 4 | 4.4396 | 19.9992 |
| -2 | 1 | 2 | 4 | 4.1791 | 21.2601 |
| -3 | 0 | 2 | 2 | 4.1648 | 21.3338 |
| -3 | 1 | 1 | 4 | 4.1089 | 21.6273 |
| 3 | 1 | 0 | 4 | 4.0786 | 21.7904 |
| 3 | 0 | 1 | 2 | 4.0720 | 21.8259 |
| 1 | 1 | 2 | 4 | 4.0376 | 22.0144 |
| 2 | 0 | 2 | 2 | 3.9388 | 22.5737 |

According to the invention, monohydrated form C of (3R,4R)-4-[3-(S)-hydroxy-3-(6-methoxyquinolin-4-yl)propyl]-1-[2-(2-thienylthio)ethyl]piperidine-3-carboxylic acid can be obtained by crystallization from mixtures of water and water-miscible organic solvents, in particular according to the following methods:

by evaporation at 20° C.–25° C., for a period of time ranging up to 7 to 9 days, of a saturated solution of the amorphous form of (3R,4R)-4-[3-(S)-hydroxy-3-(6-methoxyquinolin-4-yl)propyl]-1-[2-(2-thienylthio)ethyl]-piperidine-3-carboxylic acid in a methyl ethyl ketone/demineralized water (50/50 by volume) mixture or in a methanol or ethanol/demineralized water (50/50 by volume) mixture; or by stirring a suspension of form A at a temperature of 20° C.–25° C., in tetrahydrofuran/demineralized water (50/50 by volume), methyl ethyl ketone/demineralized water (80/20 by volume to 20/80 by volume), acetonitrile/demineralized water (50/50 by volume to 20/80 by volume) or ethanol or methanol/demineralized water (50/50 by volume) mixtures, for 5 days to about 30 days.

Form A can be obtained in particular by crystallization of purified amorphous (3R,4R)-4-[3-(S)-hydroxy-3-(6- methoxyquinolin-4-yl)propyl]-1-[2-(2-thienylthio)ethyl] piperidine-3-carboxylic acid from acetonitrile, by heating to the reflux temperature and then cooling to a temperature of 20° C.–25° C., over a period of time of at least one and one-half hours.

The purified amorphous form of (3R,4R)-4-[3-(S)-hydroxy-3-(6-methoxyquinolin-4-yl)propyl]-1-[2-(2-thienylthio)ethyl]piperidine-3-carboxylic acid can be prepared beforehand by chiral HPLC, as disclosed previously in U.S. Pat. No. 6,403,610.

Form C of (3R,4R)-4-[3-(S)-hydroxy-3-(6-methoxyquinolin-4-yl)propyl]-1-[2-(2-thienylthio)ethyl] piperidine-3-carboxylic acid is a pure monohydrate form. It exhibits the advantage of an improved degree of purity in comparison with the amorphous form of the acid and thus makes possible the preparation of pharmaceutical compositions not exhibiting an amount of impurities which are undesirable in nature or in degree. It can be used either for the preparation of pharmaceutical compositions or as purified intermediate form for the preparation of a pharmaceutical composition.

Form C is stable, as is shown by the tests carried out for the preparation of this crystalline form from methanol/water or ethanol/water (1/1 by volume) mixtures, it proved to be stable after 30 days.

The present invention also relates to the pharmaceutical compositions comprising monohydrated form C of (3R,4R)-4-[3-(S)-hydroxy-3-(6-methoxyquinolin-4-yl)propyl]-1-[2-(2-thienylthio)ethyl]piperidine-3-carboxylic acid according to the invention, in the pure state or optionally in combination with one and/or another of the other crystalline forms B or A, and/or in the form of a combination with one or more compatible and pharmaceutically acceptable diluents or adjuvants, or else the compositions prepared from the aforesaid form C.

The pharmaceutical compositions according to the invention can be used orally, parenterally, topically or rectally or as aerosols.

Tablets, pills, gelatin capsules, powders or granules can be used as solid compositions for oral administration. In these compositions, form C according to the invention is mixed with one or more inert diluents or adjuvants, such as sucrose, lactose or starch. These compositions can comprise substances other than diluents, for example a lubricant, such as magnesium stearate, or a coating intended for controlled release.

Form C can also be used for the preparation of liquid compositions for oral administration; use may be made of pharmaceutically acceptable solutions, suspensions, emulsions, syrups and elixirs comprising inert diluents, such as water or liquid paraffin. These compositions can also comprise substances other than diluents, for example wetting, sweetening or flavoring agents.

Form C can also be used for the preparation of compositions for parenteral administration. These compositions can be emulsions or sterile solutions. Use may be made, as solvent or vehicle, of water, propylene glycol, a polyethylene glycol, vegetable oils, in particular olive oil, or injectable organic esters, for example ethyl oleate. These compositions can also comprise adjuvants, in particular wetting, isotonizing, emulsifying, dispersing and stabilizing agents. Sterilization can be carried out in several ways, for example using a bacteriological filter, by irradiation or by heating. Compositions for parenteral administration can also be prepared in the form of sterile solid compositions which can be dissolved at the time of use in sterile water or any other injectable sterile medium.

Compositions for rectal administration include suppositories or rectal capsules which comprise, in addition to the active principle, excipients such as cocoa butter, semisynthetic glycerides or polyethylene glycols.

Compositions for topical administration can, for example, be creams, ointments, lotions or aerosols.

Compositions for inhalation can be in particular be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, monohydrated form C of (3R,4R)-4-[3-(S)-hydroxy-3-(6-methoxyquinolin-4-yl)propyl]-1-[2-(2-thienylthio)ethyl]-piperidine-3-carboxylic acid is finely divided and combined with a water-soluble solid diluent or vehicle with a particle size of 30 μm to 80 μm, for example dextran, mannitol or lactose.

As a whole, all these compositions exhibit the advantage of a high degree of purity of active principle.

EXAMPLES

The following examples, given without implied limitation, illustrate the present invention.

Example 1

Monohydrated form C of (3R,4R)-4-[3-(S)-hydroxy-3-(6-methoxyquinolin-4-yl)propyl]-1-[2-(2-thienylthio)ethyl]piperidine-3-carboxylic acid A suspension of approximately 460 mg of (3R,4R)-4-[3-(S)-hydroxy-3-(6-methoxyquinolin-4-yl)propyl]-1-[2-(2-thienylthio)ethyl]piperidine-3-carboxylic acid in 1.84 $cm^3$ of a water/methanol (50/50) mixture is brought to reflux until completely dissolved. The solution is cooled to approximately 20° C. The crystals which appear during cooling are filtered off and then dried at about 20° C. and normal pressure. Monohydrated form C of (3R,4R)-4-[3-(S)-hydroxy-3-(6-methoxyquinolin-4-yl)propyl]-1-[2-(2-thienylthio)ethyl]piperidine-3-carboxylic acid (436.3 mg) is obtained in the form of white crystals.

Example 2

Form A of (3R,4R)-4-[3-(S)-hydroxy-3-(6-methoxyquinolin-4-yl)propyl]-1-[2-(2-thienylthio)-ethyl]piperidine-3-carboxylic acid A solution of (3R,4R)-4-[3-(R,S)-hydroxy-3-(6-methoxyquinolin-4-yl)propyl]-1-[2-(2-thienylthio)ethyl] piperidine-3-carboxylic acid in dichloromethane is chromatographed on a column with a length of 35 cm and a diameter of 8 cm packed with 1200 g of Kromasil® silica (particle size of 10 μm). A precolumn with a length of 10 cm and a diameter of 6 cm containing 250 g of Merck silica (particle size 15–25 μm) is added to the system. Elution is carried out using a dichloromethane/methanol/acetonitrile (60/20/20 by volume) mixture. The flow rate is adjusted from 150 $cm^3$/min to 180 $cm^3$/min and detection is carried out in the ultraviolet at 280 nm. This operation, repeated three times, to treat a batch of 20 g, results in two diastereoisomers being obtained. The intermediate fractions are concentrated and reinjected into the column. The fractions corresponding to the first diastereoisomer (diastereoisomer A) are concentrated to dryness under reduced pressure (5 kPa) at a temperature in the region of 40° C. The residue is crystallized by dissolving in 60 $cm^3$ of acetonitrile, bringing the solution to reflux for 5 minutes and then cooling to a temperature of 20° C. over 1 hour 30 minutes. The crystals are filtered off, and washed twice with 20 cm³ of acetonitrile and then twice with 20 cm³ of ethyl ether. After drying in an oven under reduced pressure (13 Pa) at a temperature in the region of 40° C., (3R,4R)-4-[3-(S)-hydroxy-3-(6-methoxyquinolin-4-yl)propyl]-1-[2-(2-thienylthio)ethyl] piperidine-3-carboxylic acid (5.38 g), diastereoisomer A, is obtained in the form of white crystals (form A).

Optical rotation $[\alpha]_D^{20}=-77.80$ (in dichloromethane at 0.5%).

The form A thus obtained can be converted to crystalline monohydrated form C under the conditions described above.

What is claimed is:

1. Monohydrated form C of (3R,4R)-4-[3-(S)-hydroxy-3-(6-methoxyquinolin-4-yl)propyl]-1-[2-(2-thienylthio)ethyl] piperidine-3-carboxylic acid having a powder X-ray diffraction pattern

| h | k | l | Multiplicity factor J | Lattice spacing (Å) | 2θ "mean $\lambda_{CuK\alpha}$" 1.54184 Å |
|---|---|---|---|---|---|
| 1 | 1 | 0 | 4 | 10.0418 | 8.8058 |
| 2 | 0 | 0 | 2 | 10.0112 | 8.8327 |
| 1 | 0 | 1 | 4 | 9.6580 | 9.1564 |
| 0 | 1 | 1 | 4 | 7.9939 | 11.0679 |
| 2 | 1 | 0 | 4 | 7.5809 | 11.6729 |
| 1 | 1 | 1 | 8 | 7.4241 | 11.9204 |
| 2 | 0 | 1 | 4 | 7.4117 | 11.9404 |
| 2 | 1 | 1 | 8 | 6.2468 | 14.1776 |
| 0 | 2 | 0 | 2 | 5.8035 | 15.2666 |
| 3 | 1 | 0 | 4 | 5.7858 | 15.3136 |
| 3 | 0 | 1 | 4 | 5.7095 | 15.5195 |
| 1 | 2 | 0 | 4 | 5.5741 | 15.8990 |
| 0 | 0 | 2 | 2 | 5.5128 | 16.0771 |
| 1 | 0 | 2 | 4 | 5.3150 | 16.6795 |
| 0 | 2 | 1 | 4 | 5.1355 | 17.2667 |
| 3 | 1 | 1 | 8 | 5.1233 | 17.3084 |
| 2 | 2 | 0 | 4 | 5.0209 | 17.6641 |
| 4 | 0 | 0 | 2 | 5.0056 | 17.7185 |
| 0 | 1 | 2 | 4 | 4.9796 | 17.8116 |
| 1 | 2 | 1 | 8 | 4.9745 | 17.8301 |
| 1 | 1 | 2 | 8 | 4.8324 | 18.3588 |
| 2 | 0 | 2 | 4 | 4.8290 | 18.3719 |
| 4 | 1 | 0 | 4 | 4.5964 | 19.3104 |
| 2 | 2 | 1 | 8 | 4.5694 | 19.4256 |
| 4 | 0 | 1 | 4 | 4.5579 | 19.4752 |
| 2 | 1 | 2 | 8 | 4.4585 | 19.9134 |
| 3 | 2 | 0 | 4 | 4.3794 | 20.2770 |
| 3 | 0 | 2 | 4 | 4.2503 | 20.8996 |
| 4 | 1 | 1 | 8 | 4.2425 | 20.9387 |
| 3 | 2 | 1 | 8 | 4.0701 | 21.8363 | at 295 K expressed in terms of h, k, l, multiplicity factor J, lattice spacing in Å and 2θ.

2. Monohydrated form C of (3R,4R)-4-[3-(S)-hydroxy-3-(6-methoxyquinolin-4-yl)propyl]-1-[2-(2-thienylthio)ethyl] piperidine-3-carboxylic acid of claim 1 wherein the unit cell is orthorhombic (space group P2₁2₁2₁, Z=4) and the unit cell parameters are:

a=20.0224 Å α=β=γ=90°
b=11.6071 Å
c=11.0255 Å V=2562.36 Å³
at 295 K.

3. A process for the preparation of monohydrated form C of (3R,4R)-4-[3-(S)-hydroxy-3-(6-methoxyquinolin-4-yl) propyl]-1-[2-(2-thienylthio)ethyl]-piperidine-3-carboxylic acid comprising the steps of:

a. dissolving sufficient quantities of amorphous (3R,4R)-4-[3-(S)-hydroxy-3-(6-methoxyquinolin-4-yl)propyl]-1-[2-(2-thienylthio)ethyl]-piperidine-3-carboxylic acid in a mixture of water and a water-miscible organic solvent to provide a saturated solution, and b. evaporating said solution at 20° C. to 25° C. over a suitable period of time.

4. The process of claim 3 wherein the suitable period of time is up to 9 days.

5. The process of claim 4 wherein the suitable period of time is up to 7 days.

6. The process of claim 3 wherein the water miscible organic solvent is selected from the group consisting of methyl ethyl ketone, methanol and ethanol.

7. The process of claim 6 wherein the ratio of water to water-miscilbe organic solvent is 50/50 by volume.

8. A process for the preparation of monohydrated form C of (3R,4R)-4-[3-(S)-hydroxy-3-(6-methoxyquinolin-4-yl) propyl]-1-[2-(2-thienylthio)ethyl]-piperidine-3-carboxylic acid comprising the step of stirring a suspension of form A of (3R,4R)-4-[3-(S)-hydroxy-3-(6-methoxyquinolin-4-yl) propyl]-1-[2-(2 -thienylthio)ethyl]-piperidine-3-carboxylic acid in a mixture of water and a water-miscible organic solvent at 20° C. to 25° C. for at least 5 days.

9. The process of claim 8 wherein the mixture is stirred for at least 5 days to about 30 days.

10. The process of claim 8 wherein the water-miscible organic solvent is selected from the group consisting of tetrahydrofuran, methyl ethyl ketone, acetonitrile, ethanol and methanol.

11. The process of claim 10 wherein the ratio of water and tetrahydrofuran is 50:50 by volume.

12. The process of claim 10 wherein the ratio of water and methyl ethyl ketone is 80:20 to 20:80 by volume.

13. The process of claim 10 wherein the ratio of water and acetonitrile is 50:50 by volume.

14. The process of claim 10 wherein the ratio of water and ethanol is 50:50 by volume.

15. The process of claim 10 wherein the ratio of water and methanol is 50:50 by volume.

16. A method for treating a bacterial infection comprising administering to a patient in need of said treatment a therapeutically effective amount of monohydrated form C of 3R,4R)-4-[3-(S)-hydroxy-3-(6-methoxyquinolin-4-yl) propyl]-1-[2-(2-thienylthio)ethyl]piperidine-3-carboxylic acid.

17. A method for treating a bacterial infection comprising administering to a patient in need of said treatment a therapeutically effective amount of monohydrated form C of 3R,4R)-4-[3-(S)-hydroxy-3-(6-methoxyquinolin-4-yl) propyl]-1-[2-(2-thienylthio)ethyl]piperidine-3-carboxylic acid and form A of 3R,4R)-4-[3-(S)-hydroxy-3-(6-methoxyquinolin-4-yl)propyl]-1-[2-(2-thienylthio)ethyl] piperidine-3-carboxylic acid; or said monohydrated form C and form B of 3R,4R)-4-[3-(S)-hydroxy-3-(6-methoxyquinolin-4-yl)propyl]-1-[2-(2-thienylthio)ethyl]piperidine-3-carboxylic acid.

18. The method for treating a bacterial infection according to claim 17 comprising administering to a patient in need of said treatment a therapeutically effective amount of monohydrated form C of 3R,4R)-4-[3-(S)-hydroxy-3-(6-methoxyquinolin-4-yl)propyl-]1-[2-(2-thienylthio)-ethyl] piperidine-3-carboxylic acid and form A of 3R,4R)-4-[3-(S) hydroxy-3-(6-methoxyquinolin-4-yl)propyl]-1-[2-(2-thienylthio)ethyl]piperidine-3-carboxylic acid.

19. The method for treating a bacterial infection according to claim 17 comprising administering to a patient in need of said treatment a therapeutically effective amount of monohydrated form C of 3R,4R)-4-[3-(S)-hydroxy-3-(6-methoxyquinolin-4-yl)propyl]-1-[2-(2-thienylthio)-ethyl]

piperidine-3-carboxylic acid and form B of 3R,4R)-4-[3-(S)-hydroxy-3-(6-methoxyquinolin-4-yl)propyl-]1-[2-(2-thienylthio)ethyl]piperidine-3-carboxylic acid.

20. A method for treating a bacterial infection comprising administering to a patient in need of said treatment a therapeutically effective amount of monohydrated form C of 3R,4R)-4-[3-(S)-hydroxy-3-(6-methoxyquinolin-4-yl)propyl]-1-[2-(2-thienylthio)ethyl]piperidine-3-carboxylic acid, form A of 3R,4R)-4-[3-(S)-hydroxy-3-(6-methoxyquinolin-4-yl)propyl]-1-[2-(2-thienylthio)ethyl]piperidine-3-carboxylic acid and form B of 3R,4R)-4-[(3-(S)-hydroxy-3-(6-methoxyquinolin-4-yl)propyl]-1-[2-(2-thienylthio)ethyl]piperidine-3-carboxylic acid.

21. A process for the preparation of form A of 3R,4R)-4-[3-(S)-hydroxy-3-(6-methoxyquinolin-4-yl)propyl]-1-[2-(2-thienylthio)ethyl]piperidine-3-carboxylic acid from monohydrated form C of 3R,4R)-4-[3-(S)-hydroxy-3-(6-methoxyquinolin-4-yl)propyl]-1-[2-(2thienylthio)ethyl]piperidine-3-carboxylic acid comprising the steps of:

a. drying said monohydrated form C below 50% humidity to provide form B of (3R,4R)-4-[3-(S)-hydroxy-3-(6-methoxyquinolin-4-yl)propyl]-1-[2-(2-thienylthio)ethyl]-piperidine-3-carboxylic acid, and b. heating said form B at a temperature from about 148° C. to about 155° C. to provide form A of 3R,4R)-4-[3-(S)-hydroxy-3-(6-methoxyquinolin-4-yl)propyl]-1-[2-(2-thienylthio)ethyl]piperidine-3-carboxylic acid.

\* \* \* \* \*